United States Patent [19]

Malcosky et al.

[11] Patent Number: 4,773,255

[45] Date of Patent: Sep. 27, 1988

[54] APPARATUS FOR INJECTING GAS INTO A PIPELINE

[75] Inventors: Norman D. Malcosky; Gregory Koziar, both of Columbus, Ohio

[73] Assignee: Columbia Gas System Service Corporation, Columbus, Ohio

[21] Appl. No.: 63,969

[22] Filed: Jun. 19, 1987

Related U.S. Application Data

[62] Division of Ser. No. 790,814, Oct. 24, 1985, Pat. No. 4,690,689, which is a division of Ser. No. 471,278, Mar. 2, 1983, Pat. No. 4,551,154.

[51] Int. Cl.$^4$ .............................................. G01M 3/04
[52] U.S. Cl. .................................. 73/40.7; 48/196 R; 436/29
[58] Field of Search ................. 73/40.7, 155; 222/334; 137/596.18; 436/3, 25, 27, 28, 29, 56,; 340/606; 48/193, 195, 196 R

[56] References Cited

U.S. PATENT DOCUMENTS

| | | | |
|---|---|---|---|
| 2,032,431 | 3/1936 | Odell | 48/195 |
| 2,894,478 | 7/1959 | Reed | 48/195 |
| 3,016,089 | 10/1963 | Scott et al. | 48/193 |
| 3,523,771 | 8/1970 | Anderson | 48/195 |
| 3,714,421 | 1/1973 | Josias et al. | 250/381 |
| 4,052,555 | 10/1977 | Mears et al. | 252/372 |
| 4,156,813 | 5/1979 | Flanagan et al. | 250/381 |
| 4,173,141 | 11/1979 | Kissell et al. | 73/40.7 |
| 4,328,700 | 5/1982 | Fries | 73/40.7 |
| 4,353,249 | 10/1982 | Lagus et al. | 73/155 |
| 4,420,565 | 12/1983 | Schmitt | 436/27 |
| 4,501,324 | 2/1985 | Sandiford et al. | 436/27 X |

FOREIGN PATENT DOCUMENTS 145186 11/1980 Fed. Rep. of Germany ........ 73/155

OTHER PUBLICATIONS

Chemical Abstract No. 42885b, vol. 68, 1968.
Chemical Abstract No. 38380k, vol. 75, 1971.
Peterson et al., Technical Bulletin 79-1, "In Situ Characterization of Permeability Porosity, and Communication in Underground Regions Systems, " Science and Software, May 1979.
Timko et al., SF$_6$ Adds a New Dimension to Mine Ventilation Analysis Engineering and Mining Journal, Feb. 1984, pp. 50-51.
Cecala et al., How Gassy Non Coal Mines can Simulate Methane Flow, Engineering and Mining Journal, Feb. 1984, pp. 51-52.

Primary Examiner—Jerry W. Myracle
Attorney, Agent, or Firm—Sidney W. Millard

[57] ABSTRACT

The invention provides a method for tagging methane by adding thereto one or more of the tracer compounds sulfur hexafluoride and chloropentafluoroethane. The methane being tagged is normally being stored in underground storage fields to provide identity and proof of ownership of the gas. The two tracer compounds are readily detectable at very low concentrations by electron capture gas chromatography apparatus which can be made portable and thus suitable for use in the field.

14 Claims, 2 Drawing Sheets

APPARATUS FOR INJECTING GAS INTO A PIPELINE

This is a divisional case of Ser. No. 790,814, filed Oct. 24, 1985, now U.S. Pat. No. 4,690,689 which is a division of Ser. No. 471,278, filed Mar. 2, 1983, now U.S. Pat. No. 4,551,154.

BACKGROUND OF THE INVENTION

This invention relates to a gas tracer composition and method. More specifically, this invention relates to methods for the tagging of methane and to tagged methane compositions. The term "methane" is used herein to denote not only pure methane, but also to natural gas compositions which are mainly methane but may contain minor proportions of other gases, for example helium, ethane and hydrogen sulfide. The term "methane" as used herein also extends to so-called synthetic natural gas i.e. methane produced by chemical synthesis and intended to be used as a replacement for natural gas. "Methane" may also refer to liquified natural gas (LNG) as it is produced either domestically or overseas. LNG is made by the pressurized and cooling liquifaction process as it is performed on natural gas coming out of the ground.

The demand for natural gas is of course largely seasonal, because much of the natural gas is consumed for heating purposes. Since it is desirable to maintain a steady output from gas wells throughout the year, it is necessary to store enormous quantities of natural gas during the warmer months of the year in order to meet the peak winter demands, thereby to allow proper matching of the relatively steady production of natural gas against the fluctuating demand therefor. Because of the enormous quantities of gas (of the orders of billions of standard cubic feet) which have to be stored, the construction of artificial storage facilities for the gas is economically unattractive, and most of the gas is thus stored in natural formations, primarily exhausted natural gas production fields, though salt domes may also be used.

The geology of the exhausted gas fields used for storage may be both complex and not entirely known; for example, unknown to the operators there might be underground communication between an exhausted gas field used for storage and a nearby field which is still being used for production. Furthermore, there is a possibility that someone else drilling in the vicinity may penetrate the gascontaining formations during drilling operations, and proceed to produce gas from the storage field, thereby (knowingly or unknowingly) stealing gas from its rightful owner. Accordingly, it is very desirable that the owner of the gas being stored in a gas storage field be able to "tag" the gas by adding a minor proportion of a tracer compound thereto, so that should the gas placed in the storage field migrate to a nearby field or be removed by unauthorized persons it can be identified; it will be appreciated that generally natural gas is a fungible product and, absent the addition of some tracer compound thereto, it is not possible to determine the source of any particular sample of natural gas.

Hitherto, the main tracer compound used to tag methane has been ethylene. Until recently, ethylene was thought to be a good tracer compound because it moves through a gas field in a manner very similar to methane (and thus does not become separated from the methane as the methane diffuses through large gas fields) and because it was thought not to occur in natural methane supplies. Furthermore, even very small amounts of ethylene are easily detectable in methane. Unfortunately, it has now been discovered that although ethylene does not occur naturally as a contaminant of methane, there are at least two ways in which methane may be contaminated with traces of ethylene even though it has not been deliberately tagged wtih ethylene. Firstly, some fields now used for methane storage have previously been used for storing coke-oven gas, which contains considerable amounts of ethylene. The storage of coke-oven gas in these fields has left a residue of ethylene within the fields, so that methane supplies pumped into such fields do become contaminated with this residual ethylene. Secondly, some of the processes by which natural gas fields are prepared for use as either storage or production facilities produce ethylene; in particular, treatment of gas wells with acid to clean and open casing perforation results in contact of the acid with the steel in the well pipe, thus producing trace quantities of ethylene. Accordingly, ethylene is no longer useful as a reliable tracer compound, and there is thus a need for other tracer compounds for tagging methane.

The selection of appropriate tracer compounds for use in tagging methane supplies presents very considerable difficulties, in view of the very exacting requirements which a tracer compound must meet. Firstly, the tracer compound must be one which does not occur even in minute quantities in natural supplies of methane, which may contain a variety of contaminants including the inert gases, hydrogen sulfide, ethane, propane and other hydrocarbons. In addition, the tracer compound must diffuse through a gas storage field in a manner very similar to that of methane, otherwise if a single injector well or a small cluster of injector wells are used to inject gas into a large storage field, the tracer may remain in the vicinity of the injector well(s), leaving gas at large distances from the injector wells effectively untagged. Since many gas storage fields contain traces of liquid hydrocarbons, the tracer compound must not be too soluble in such hydrocarbons, otherwise the tracer will be absorbed by the liquid hydrocarbons, again leaving the gas stored in the field untagged. The tracer compound must be stable for periods of at least several months in the presence of methane and any possible impurities in natural methane supplies. Moreover, in view of the enormous volumes of gas which have to be tagged (a single natural gas field may typically store ten to fifty billion standard cubic feet (Bscf) of methane) and the difficulties which may be encountered in transporting large quantities of tracer compounds to the gas storage fields, economic considerations dictate that any tracer compound be detectable in concentrations of no more than a few parts per million in methane. Since investigations of unauthorized removal of tagged natural gas from a storage field may require analysis of the suspect gas in the field, the tracer compound must be detectable at such very low concentrations in methane using readily portable apparatus. Finally, since it is not practicable to remove the tracer compound from the methane after it has been withdrawn from storage, the tracer compound must not interfere with or create dangers during any of the normal uses of methane.

It should be noted that the provision of tracer compounds for methane stored in gas storage fields involves very different problems from the provision of tracer compounds which are used to detect leaks in gas pipelines. When it is desired to use a tracer compound to find the position of a leak in a gas pipeline, only a relatively small amount of gas flowing through the pipeline has to be tagged, and thus it is practical to use much higher concentrations of tracer compounds. Indeed, since the leaking pipeline is frequently shut down, it may be possible to fill the pipeline with the "tracer" compound in order to produce the maximum possible concentration of tracer compound adjacent the leak. Thus, many techniques for detecting leaks in pipelines are totally inapplicable to tagging gas stored in storage fields. Furthermore, tracer compounds used for detecting leaks in pipelines do not have to meet the requirements of (1) having a mobility through rock, (2) not dissolving in hydrocarbons and (3) being stable for months at a time, which a tracer compound intended for use in gas fields must meet. For this reason, most of the tracer compounds suggested for use in detecting leaks from pipelines are totally unsuitable for use in tagging methane to be stored in gas storage fields. For example, U.S. Pat. No. 3,523,771, granted Aug. 11, 1972, to Anderson, describes a process for detecting leaks from pipelines in which there is added to a fuel gas passing through the pipeline from 0.01 to 10% by weight of certain organometallic compounds which react spontaneously with air to produce a smoke visible at the source of a leak in a pipeline. The use of these organometallic compounds as tracers in gas fields would be entirely inappropriate since the amount of tracer which would have to be added would be so large as to be economically impracticable, and in any case, gas recovered from a natural gas storage fields almost never comes into contact with air. Furthermore, it is most unlikely that such organometallic compounds would diffuse through a gas storage field at the same speed as methane, and, as described in U.S. Pat. No. 3,523,771, the addition of organometallic compounds to the field gases does present serious problems in later using the fuel gases unless that organometallic compounds are removed; while it is practicable to remove the organometallic compounds from the relatively limited amount of gas which has to be tagged for leak detection purposes, it is utterly impractical to attempt to remove a trace of compound from the huge quantities of gas recovered from a gas storage field. Accordingly, although the process described in U.S. Pat. No. 3,523,771 may be a useful method of tagging fuel gases to detect leaks in pipelines, it is entirely impractical as a method of tagging gas to be stored in a gas storage field.

After extensive evaluation involving over 140 potential tracer compounds, we have now discovered two new tracer compounds for methane which meet all the aforementioned requirements.

SUMMARY OF THE INVENTION

This invention is based upon the discovery that sulfur hexafluoride and chloropentafluoroethane meet the requirements set forth above for tracer compounds for use in tagging methane. Both compounds are readily detectable at concentrations of a few parts per million or below by electron capture gas chromatography.

Accordingly, in one aspect this invention provides a method for tagging methane comprising adding to the methane a minor proportion of sulfur hexafluoride or chloropentafluoroethane (Freon-115).

A further aspect of the invention is a tagged methane composition comprising methane and a minor portion of sulfur hexafluoride or chloropentafluoroethane.

Finally, the invention provides a method for tagging methane in an underground storage field which comprises adding to the methane to be stored in the field a minor proportion of the tracers and pumping the tagged methane into the underground storage field via an injection well.

DETAILED DESCRIPTION OF THE INVENTION

Although the methods of the instant invention are primarily intended for the tagging of gaseous methane in underground storage fields, the invention is also applicable to tagging methane in other forms. For example, it may be used to tag methane stored in aboveground pressurized storage tanks, and liquified methane in road or rail tankers, liquified natural gas storage tanks or liquified natural gas transport ships.

The two tracer compounds used in the instant method, sulfur hexafluoride and chloropentafluoroethane and may be used either singly or in combination. Indeed, it is one of the advantages of the instant invention that, by providing a plurality of tracer compounds and combinations of tracer compounds, it enables different masses of gas to be labeled differently. For example, in certain circumstances where two gas storage fields lie adjacent one another, it may be desired to label the gas in the two fields differently, and the instant invention renders it possible to do so.

The utility of sulfur hexafluoride and chloropentafluoroethane as tracer compounds is due to their easy detection at very low concentrations by various gas chromatography techniques. One method used was flame ionization chromatography which is effective for detecting ethylene. Thermal conductivity chromatography can also be used in detection of chloropentafluoroethane and sulfur hexafluoride, however detection of sulfur hexafluoride by thermal conductivity chromatography is more difficult when the concentrations are very low. Accordingly, the preferred method of analyzing for the presence of sulfur hexafluoride is electron capture gas chromatography. Electron capture gas chromatographic techniques are especially effective in the detection of good electron receiving molecules such as chloropentafluoroethane and sulfur hexafluoride, however ethylene is not capable of detection by electron capture gas chromatographic procedures. Electron capture gas chromatographs are available commercially which are sufficiently compact and lightweight to be easily transported in a vehicle and which can give good results under field conditions. Using such electron capture gas chromatographs, we have found that sulfur hexafluoride is detectable at a minimum concentration of about 5 parts per trillion and chloropentafluoroethane at a minimum concentration of about 0.35 parts per million. Because sulfur hexafluoride can be detected at low concentrations, and thus much less tracer compound is required to tag a given quantity of gas, it is the preferred tracer for use in the instant method. Although the tracer compound should of course be added to the methane at a concentration considerably greater than the minimum concentration, to allow for some dilution of the tagged methane by other methane which may be present in the storage and to allow for more reliable detection or sites, the amount of sulfur hexafluoride needed for proper operation of the instant method is very small; we prefer to use sulfur hexafluoride as a tracer compound in an amount not exceeding about five parts per billion of the methane by volume, and the optimum concentration of sulfur hexafluoride appears to be about 500 parts per trillion by volume. In contrast, we prefer to use chloropentafluoroethane in an amount not exceeding about 20 parts per million of methane by volume, and most desirably about four parts per million by volume.

Figure 2:
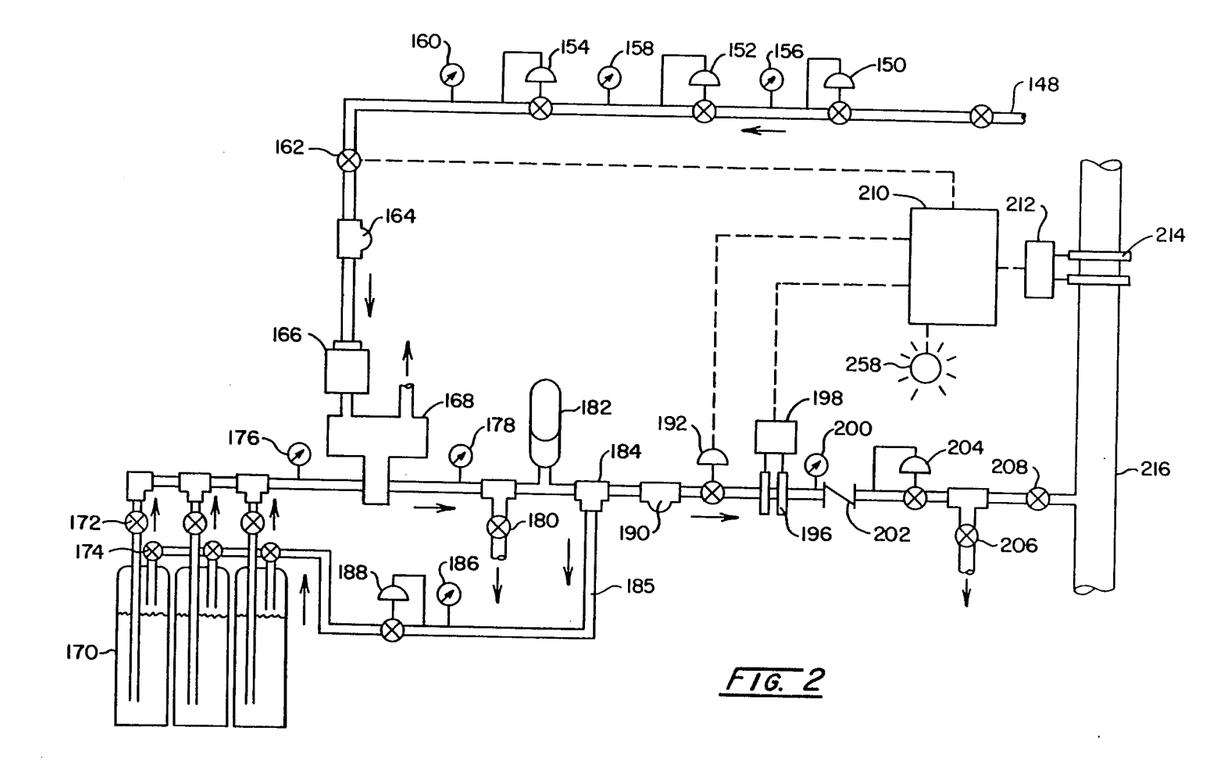
FIG. 2 is a schematic of the apparatus for use in a liquid injection system according to the present invention.

The exact method by which the tracer compound is mixed with the methane is not crucial. For example, a gaseous stream of the tracer compound could be mixed directly with a gaseous stream of methane being pumped into an underground storage field. However, because injection wells for underground gas storage fields may be in relatively remote areas, and thus it may be necessary for apparatus adding the tracer compound to methane being pumped into the storage fields to run unattended for several days, to reduce the capital cost and physical volume of the apparatus for storing and injecting the tracer compound, we have found it convenient to store both tracer compounds in liquid form and to add them to the methane as a mist of liquid tracer compound which of course rapidly evaporates to form a homogeneous mixture of tracer compound and methane. The provision of suitable liquid pumps for pumping appropriate quantities of chloropentafluoroethane does not present any problems, since the quantities of this tracer which need to be added to a typical natural gas stream entering a storage field are sufficiently large to be well within the pumping range of commercially-available pumps suitable for field use. However, the preferred concentrations of sulfur hexafluoride tracer are so low that a typical methane flow into an underground gas storage field only requires the addition of about 5 ml. per day of sulfur hexafluoride as tracer compound, and it is difficult to find pumps suitable for field use which can pump liquid sulfur hexafluoride at this extremely low rate. Moreover, at such low flow rates even very small leaks may cause serious problems and, if even a modest length of tubing is positioned between the sulfur hexafluoride source and the gas pipeline, the tracer will take a long time to reach the pipeline and tag the gas therein. Accordingly, in may cases it will be found more convenient to add sulfur hexafluoride tracer to methane in the form of a liquid solution of sulfur hexafluoride in a liquid solvent, such as methanol or carbon dioxide, in order to dilute the sulfur hexafluoride and allow for pumping of liquid at a rate which is more suitable for commercially available field-usable pumps. Carbon dioxide needs to be maintained at a pressure of 900 psi in order to be capable of liquifaction at reasonable room temperatures; however, carbon dioxide has been found to be a very effective carrier and no stratification of sulfur hexafluoride in a liquid solution with carbon dioxide has been found even following months of storage. FIG. 2 depicts schematically an equipment arrangement suitable for the injection of sulfur hexafluoride in a liquid solution with carbon dioxide as a tracer gas directly into a methane pipeline. The same equipment arrangement can be utilized for the injection of chloropentafluoroethane which occurs as a liquid at room temperature without the necessity of it being resolved in a carrier liquid.

FIG. 2 shows schematically an apparatus being used to carry out the instant method. This apparatus includes a gas supply line 148 in a pipeline 216 via which gas in provided from a pipeline (alternatively the line 148 could be connected to a gas field).

Regulators 150, 152 and 154 progressively reduce and maintain the pump operating gas to a operable pressure of around 75 psig from the normal pipeline pressure of 600 to 1400 psi. Pressure gauges 156, 158, and 160 reflect the various pressures that are being controlled by their respectively regulators. A solenoid valve 162 is controlled from a main controller unit which allows for the unsupervised operation of the system; solenoid valve 162 is turned to an off position at times during which the pump is not to be operated. An in-line filter 164 is provided simply to clean the gas. From the filter 164, the gas passes through a pump controller 166 and thence to a gas-powered liquid pump 164 of the positive displacement type, which is controlled by the controller 166. After being used to drive the pump, excess gas is simply vented to the atmosphere. The tracer in a liquid form, either sulfur hexafluoride dissolved in liquid carbon dioxide or chloropentafluoroethane, is stored in bottles 170. The concentration of sulfur hexafluoride in the liquid solution is predetermined based upon the size of the field being injected or the amount of gas to be tagged and is shipped to the field already made up in appropriate concentration. When the chloropentafluoroethane is utilized it is used in a pure liquid form without a diluent liquid, the pump and its controller systems being capable of correctly metering the required amounts without the benefit of a diluting liquid. The liquid is withdrawn from bottles 170 through isolation valves 172 by pump 168. A pressure gauge 176 is provided to indicate the pressure at the outlet from the bottles 170 and is especially necessary when liquid carbon dioxide is utilzied as the diluent liquid since a pressure of at least 900 psig must be maintained in such a carbon dioxide diluted system. A further pressure gauge 178 provides visual indication of the output pressure of the pump which must be high enough to allow injection into the field and also sufficiently high to be properly regulated by a flow control valve 192 described below. Downstream of the pressure gauge 178, a vent line 180 is provided for purging the line of air during start-up of the pump 168. Next, an accumulator 182 is provided to smooth flow along the line and reduce the variations in flow caused by the discrete strokes of the positive displacement pump 168. A bypass line 185 branches from the pump outlet line at 184 to return unused tracer liquid to the bottles 170 for recirculation. This by-pass line 185 incorporates a regulator 188 and an associated pressure gauge 186 to ensure that tracer liquid is recirculated via line 185 only when the amount of tracer liquid supplied by the pump 168 is in excess of that required for tagging purposes. From the branch point 184, the tracer liquid passes through a filter 190 and thence to the flow control 192; the filter 190 serves to prevent obstruction of the flow control valve 192. The flow control valve 192 is controlled by a controller unit 210 so as to meter the appropriate amount of liquid; thus the flow of tracer liquid can be regulated from a very low flow or no flow all the way to metering in the proper tagging amounts for full flow in the pipeline 216. The controller unit 210 additionally takes data from flow meters 196 and 214 having differential pressure cells 198 and 212 respectively in order to regulate the amount of tracer liquid being passed by flow control valve 192 based upon actual flow measurements both in the main line and in the tracer line. The controller 210 is provided with a visual and audio alarm 258 to indicate when there is flow through the pipeline but no flow through the gas tracer line, thus indicating failure of the gas tagging system. The pressure at flow control valve 192 is maintained such that there is sufficient "subcooling" of the tracer liquid that no flashing of the liquid occurs in the control valve which is generally a high-pressure drop device. Flashing of the liquid would render useless the measurements by flow meter 196 and would not allow sufficient control of the tracer volumes in order to be assured of economical gas tagging. A pressure gauge 200 measures the pressure of the tracer liquid downstream of the flow control valve 192. A regulator 204 steps down the pressure to an appropriate value for injection directly into the gas pipeline 216. A check valve 202 disposed between the pressure gauge 200 and the regulator 204 prevents backflow from the pipeline 216 back into the system especially during periods when no tracer is being injected. A vent line 206 vents any excess pressure found in the last leg of the line, while an isolation valve 208 isolates the entire liquid injection system from the pipeline 216.

Figure 3:
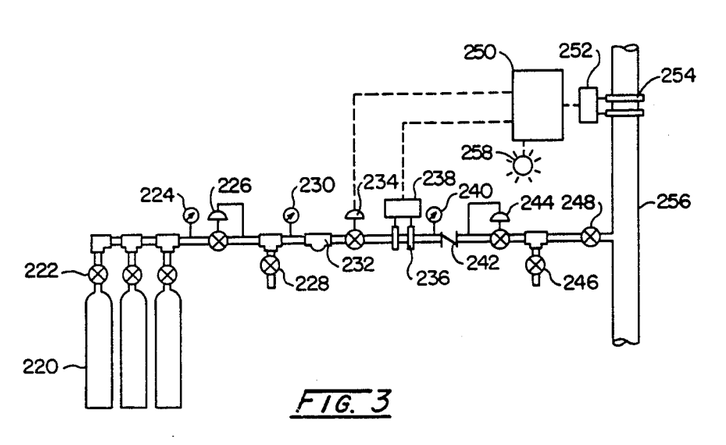
FIG. 3 is a schematic of the apparatus for gaseous injection system according to the present invention.

Additionally sulfur hexafluoride may be injected in a gaseous form utilizing a diluent gas, preferably nitrogen. FIG. 3 depicts schematically the apparatus that may be utilized for gaseous injection of sulfur hexafluoride dissolved in gaseous nitrogen as a tracer gas into a gas pipeline 256. The mixed gas sulfur hexafluoride and nitrogen is stored in bottles 220 which are shipped to the field in a predetermined concentration based upon the amount of gas to be tagged or the size of the reservoir to be tagged. Isolation valves 222 are used to prevent the escape of gas from the bottles until it is required by the system. The pressure of the bottles may be observed on a pressure gauge 224 which is associated with the inlet side of a gas regulator 226. A vent 228 is provided to prevent inadvertent overpressurization and also to vent the line after an injection has been completed. The pressure in the gas line after reduction of pressure by a regulator 226 is indicated by a pressure indicator 230. An in-line filter 232 is provided to protect a flow control valve 234 from foreign matter. Gas flow control valve 234 is controlled by a controller 250 which receives gas flow information from both the pipeline and from the gas being injected through the tagging system. Flow meters 236 and 254 and their associated differential pressure gauges 238 and 252 provide such flow information directly to the controller 250. The controller 250 is also provided with a visual and audio noflow alarm 258 to indicate conditions when there is flow through the main line but no flow through the gas tagging line. This is necessary so that an operator making his rounds in the field may be aware of the fact that there is no tagging gas being injected into the main gas stream even though such tagging gas may be required. It is necessary that such an alarm be a lock-in alarm if this is an unattended injection station which it is anticipated will be the overwhelming use of such injection equipment since such injection points are usually at remote places. Downstream in the injection line from the flow meter 236 is pressure gauge 24 which indicates the downstream pressure after the flow control valve 234. Check valve 242 prevents backflow from the main line into the injection piping network while regulator 244 isolates the tracer injection system from fluctuations of pressure in the main gas line. Vent 246 is provided to vent that portion of the system downstream of the check valve 242, while an isolation valve 248 is provided to isolate the entire gas injection system piping network from the pipeline 256.

When the instant method is being used to tag methane in an underground storage field, the tracer compound may be added continuously to all the methane as it is pumped into the storage field. Alternatively, only a "slug" of methane being pumped into the storage field may be labeled, leaving the tracer to diffuse from that slug throughout the storage field. Obviously, when only part of the methane pumped into the storage field is labeled, the concentration of tracer compound added to that slug should be made sufficiently large that a regularly detectable concentration of tracer is present after the tracer has become uniformly diffused throughout all the methane in the storage field.

Figure 1:
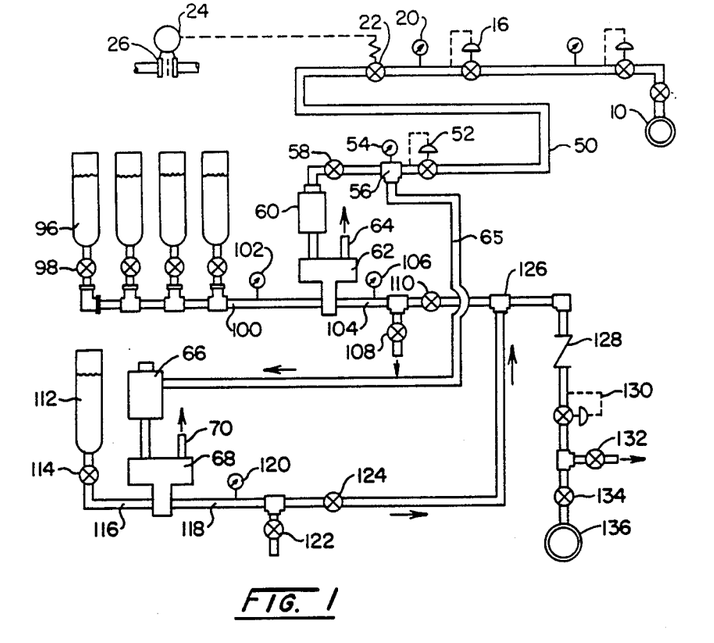
FIG. 1 is a schematic of the apparatus used for adding tracer compounds to methane during the testing period.

FIG. 1 shows schematically the apparatus used during testing for injecting tracers into methane being stored in an underground storage field. The apparatus was located adjacent the central compressor station which supplied gas under pressure to the one or more injection wells used for injecting gas into the storage field. A high-pressure gas tap to gas at about 1,000 psi. was connected on the upstream side of the tracer injection apparatus and pressurized methane therefrom passed through gas pressure regulators, which reduced the pressure of the gas in a pipe 10 to about 200 psi.

After passing a pressure regulator 16 and its accompanying pressure guage 20, the methane gas from the pipeline was then passed through a solenoid valve 22, which enabled the flow of gas from the pipeline to be cut off when injection of gas into injection wells ceased, so terminating tracer injection. For this purpose, the solenoid valve 22 was connected electrically to a differential pressure switch 24 measuring the pressure differential (and thus flow rate) through an orifice 26 located adjacent an injection well. When the pressure differential across the orifice 26 fell below 12 inches water column pressure, the solenoid valve 22 was closed, thus shutting down the tracer injection apparatus.

The stream of gas passes via the line 50 to a pressure regulator 52, which reduces the gas pressure in the line to about 50 psi. A pressure gauge 54 is provided downstream of the pressure regulator 52 in order to enable this pressure to be checked. Downstream of the pressure regulator 52, the gas stream is divided by a T-piece 56 into two streams, one of which passes via a valve 58 and a pump controller 60 to a pump 62, which controls the flow of chloropentafluoroethane. The gas leaves the pump 62 via a vent 64.

The other stream of gas from the T-piece 56 passes via a line 65 through a pump controller 66 to a pump 68 which controls the flow of sulfur hexafluoride. The gas leaves the pump 68 via a vent 70.

In this apparatus, the tracer compounds are injected into the methane flow in the form of liquids, and accordingly, each of the pumps 62 and 68 is a high-pressure piston-type positive displacement chemical feed pump of a standard commercial type which uses natural gas from the line 10 as the pneumatic driving fluid. The pump controllers 60 and 66 allow the throughput of the pumps 62 and 68 respectively to be varied from full flow to near zero by changing the piston stroke length and the pump speed.

The apparatus required for injection of chloropentafluoroethane and sulfur hexafluoride is simple, since both of these compounds can be maintained in a liquid form in a closed container without refrigeration. The chloropentafluoroethane is stored in liquid form under a pressure of about 120 psi. in several large bottles 96, each equipped with a manually operable valve 98, which enables each bottle to be cut off from the remainder of the apparatus when it is necessary to remove any particular bottle for replacement. Each of the valves 98 opens into a collecting line 100, the pressure within which is monitored by a pressure gauge 102. The line 100 feeds directly to the inlet side of the pump 62, which boosts the pressure of the liquid chloropentafluoroethane to about 1,500 psi. and discharges it into a line 104 equipped with a pressure guage 106, a relief valve 108 and a manually operable valve 110.

The sulfur hexafluoride is stored in liquid form in a small bottle 112, which holds less than one pound (450 g.) of the tracer compound. From the bottle 112, the sulfur hexafluoride passes via a manually operable valve 114 and a line 116 to the inlet side of the pump 68, which boosts its pressure to about 1,500 psi. and feeds it into a line 118 equipped with a pressure gauge 120, a relief valve 122 and a manually operable valve 124. It will be appreciated that the manually operable valves 110 and 124 allow each of the tracers to be switched on and off as desired, thereby enabling any desired combination of the two tracers to be injected.

The lines 104 and 118 carrying the tracer compounds under pressure merge at a T-piece 126, at which the tracers are mixed. From this T-piece 126, the supply of tracers under pressure passes through a check valve 128 (which serves to prevent reverse flow of methane into the tracer apparatus should the pressure within the lines 104 and 118 be insufficient), a back-pressure regulator 130, a relief valve 132 and a manually operable valve 134. The mixed tracers are finally discharged at 136 into the pipeline supplying gas to the injection well, the tracers being fed into the pipeline at a point downstream of the point at which the driving methane gas for the apparatus is tapped. The pipeline into which the combined tracers are discharged at point 136 is a 24 inch (60 centimeter) pipeline feeding all the injector wells within a particular field. It will be appreciated that the test injection apparatus is fully functional on any sized gas line.

Although sulfur hexafluoride is the most expensive tracer compound on a per unit weight basis, it is considerably cheaper in practice than the other two tracer compounds. For example, to tag two billion standard cubic feet of methane with sulfur hexafluoride at the preferred concentration of 500 parts per trillion uses only 0.4 pound of the compound, which at the commercial price of $12.40 per pound costs only $4.96. In contrast, to tag the same amount of gas using chloropentafluoroethane at the preferred concentration of four parts per million requires 3,333 pounds of the tracer compound. At the commercial price of $2.04 a pound at which this compound is sold under the trade name Freon-115 by E. I. DuPont Company, this tracer costs $6,800.

EXAMPLE I

Using test injection apparatus similar to that described above, and as shown in FIG. 1, sulfur hexafluoride and chloropentafluoroethane tracers were injected simultaneously into methane being introduced via a single injection well into an underground gas storage field. To compare the performance of these tracer compounds with that of the prior art tracer ethylene, ethylene was also added to the methane being pumped into the field. Two other wells in the same field were shut off by blind flanges and checked daily for arrival of the tracers. One of these shutin wells was approximately 500 feet east of the injection well, while the other was approximately 500 feet north of the injection well. Over the course of 10 days, approximately 42.5 million cubic feet of tagged methane was injected into the injection well. Although the concentration of the tracers varied somewhat from time to time due to experimental difficulties, the average tracer concentrations in the injected gas were 36.4 parts per billion of sulfur hexafluoride, 3.5 parts per million of chloropentafluoroethane and 73 parts per million of ethylene.

Before each daily test of the gas in each of the two recovery wells, as in the tubing stream of each well was removed to obtain a fresh sample of reservoir gas. A sample of the reservoir gas from each well was then analyzed by electron capture gas chromatography using an Analytical Instrument Development, Inc., Model 511-06 dual-column gas chromatograph having a twelve foot chromosorb 102 column and a six-foot molecular seive (5A) column which sufficed to differentiate between sulfur hexafluoride and chloropentafluoroethane. Ethylene which is not detectable by electron capture gas chromatography was analyzed by using the same gas chromatograph as is above described in conjunction with a 12 foot Chromosorb 102 column with a Hydrogen Flame Ionization Detector.

None of the tracer compounds was detected in either of the recovery wells during the first seven days of the experiment. On the 8th, 9th, and 10th days of the experiment, sulfur hexafluoride was recovered from one recovery well at concentrations of 8, 13, and 10.5 parts per billion respectively, and from the other recovery well at concentrations of 19, 15, and 17.5 parts per billion respectively. The corresponding figures for days 8, 9, and 10 of the experiment for ethylene were 5, 5, and 7 parts per million respectively in the first recovery well and 5, 5, and 21 parts per million respectively in the second recovery well. Chloropentafluoroethane tracer was detected in both recovery wells on days 8, 9, and 10 of the experiment; on day 8 the first recovery well showed only a trace of this tracer, on day 9 the concentration of chloropentafluoroethane were 0.16 parts per million, while no measurements were made on day 10 for the first recovery well. In the second recovery well, the concentrations of chloropentafluoroethane tracer were 0.5 and 0.75 parts per million on days 8 and 9 respectively; again, no measurements were made on day 10.

These results show that the two tracers used in the instant method move through the gas storage field at essentially the same speed as ethylene. In fact, the results appear to indicate that sulfur hexafluoride and chloropentafluoroethane more closely match the speed of movement of methane through the field than does ethylene, since once these two tracers hvae appeared their concentration is reasonably constant, whereas the ethylene, particularly in the second recovery well, was observed at relatively low concentrations before increasing to its final concentration, thus indicating that ethylene was "tied up" in the reservoir where sulfur hexafluoride and chloropentafluoroethane were not similarly tied up in the reservoir. The results also indicated that much smaller tagging concentrations of sulfur hexafluoride would have sufficed as tracer, since the amounts of sulfur hexafluoride measured at the recovery wells were at least two orders of magnitude greater than the minimum concentration at which sulfur hexafluoride was detectable by the apparatus used.

EXAMPLE II

In this experiment which again utilized the test injection equipment schematically shown in FIG. 1, the gas storage field used had only a single well which was used for both injection and withdrawal of the gas. In order to quantify the amount of tracer compounds which could be recovered from the reservoir, and the mixing of tagged and untagged gas within the reservoir, a slug of 308 thousand standard cubic feet of gas containing (on average) 3 parts per trillion of sulfur hexafluoride and 0.6 parts per million of chloropentafluoroethane was injected into the well; thereafter 840 thousand cubic feet of untagged methane was injected into the field over a period of 16 hours, the injection rate thus being 1.75 million standard cubic feet per day. After injection had finished, the gas was allowed to remain in the field for twelve hours and then gas was withdrawn and continuously monitored for the presence of the two tracers in order to determine the total amount of gas containing detectable concentrations of the two tracers and the proportion of the tracer injected which is recovered.

Sulfur hexafluoride was found to be the most mobile tracer, being found in 329% more gas than originally tagged. Sulfur hexafluoride also showed a good recovery rate, 86% of the tracer injected being recovered. Chloropentafluoroethane was detected in 294% more gas than was originally tagged, and at a recovery rate of 60%.

These results indicate that the tracers are somewhat less mobile than ethylene, since in similar earlier tests with ethylene, ethylene was found in 650% more gas than was originally tagged and showed substantially complete recovery.

In a second test, 411 thousand cubic feet of tagged gas containing 640 parts per trillion of the sulfur hexafluoride and 3.3 parts per million of chloropentafluoroethane was injected into the field during a period of four hours, and gas was withdrawn after only two hours delay. Because of the conditions, relatively little diffusion of the tracers into untagged gas occurred; the sulfur hexafluoride was detected in 75% more gas than tagged, the chloropentafluoroethane in 69% more gas than tagged. Reasonably good recovery was achieved for both tracers, the recovery rate being 80% for sulfur hexafluoride and 61% for chloropentafluoroethane. Ethylene gives substantially complete recovery under similar conditions.

Finally, in a third test 228 thousand standard cubic feet of tagged gas containing 90 parts per trillion of sulfur hexafluoride and 0.44 parts per million of chloropentafluoroethane were injected into the field over a period of four hours, then the field was left unchanged for 98 days. During this lengthy period of storage, all the candidates tracers showed considerable diffusion into untagged gas; upon withdrawal, the sulfur hexafluoride was found in 477% more gas than originally tagged while the chloropentafluoroethane was each found in 208% more gas than originally tagged. Sulfur hexafluoride and chloropentafluoroethane showed apparent recovery rates of 193% and 170% respectively (presumably the surplus was due to these tracers remaining from the earlier tests).

This third test shows that sulfur hexafluoride and chloropentafluoroethane have good permanence within gas storage fields, and thus are eminently suitable for tagging gas which may have to be stored for months within such field. All the tracers tested showed considerable movement into untagged storage area of the reservoir during this long term test, but the significantly lower recovery rate for nitrous oxide appears to indicate that this tracer is "tied up" to some extent in the storage formation.

As a result of the foregoing tests, the following conclusions were reached:
1. Sulfur hexafluoride shows consistently high recovery rates and does not appear to be absorbed or removed from the gas phase in any significant quantities even after lengthy storage.
2. Chloropentafluoroethane shows good permanence in the long term test, comparable to that obtained with sulfur hexafluoride.
3. Both tracers appeared to be somewhat less mobile than ethylene, but the test results indicated that they would all move satisfactorily through a gas field with the methane with which they were injected.

All of the analysis of tracer concentrations was done using the same analytical apparatus described in Experiment I above. The samples were taken in the field by bottle sample and were taken to the laboratory for analysis utilizing the equipment described. However a mobile apparatus utilizing the same basic equipment became available during the course of the testing and was utilzied for the last few tests. It is anticipated that a mobile test unit of simple construction comprising the general pieces of apparatus described at the pertinent point in Examples I above will be utilized in all future testing and it would be anticipated that line analysis in actual operations work would be done by such mobile equipment.

EXAMPLE III

Additional testing was done to determine the ability of the tracer gases to diffuse through and mix with other gas already being stored in an underground storage structure. The injection occured into a number of wells in a large field. The injection wells were isolated from the other wells in the field by placing blind plates in the inner connecting surface piping to ensure that any tracer arrivals at any of the withdrawal wells would be through the reservoir rather than via the surface piping. Preventing contamination via surface piping is a very important consideration since such trace amounts of the tracer gases are required to do the tagging operation in the first place. The simple presence of these tracer compounds in the piping can more than contaminate a withdrawal sample.

Initially, 2.8 billion cubic feet of methane tagged with the tracers was injected into the field. This was followed by an injection of 7.7 billion cubic feet of completely untagged gas, giving a total of 10.5 billion cubic feet being injected into the underground structure. The withdrawal wells were located considerable distances away from the injection wells toward the periphery of the field. The withdrawals were not begun for a period of about five months. During the time immediately prior to the withdrawal cycle there were definitive detections of the tracers in concentration near some of the withdrawal wells. The tracer sulfur hexafluoride was detected in six wells while the tracer chloropentafluoroethane was detected at only four of the well sites, sulfur hexafluoride being detected at all of the wells where chloropentafluoroethane was detected while the reverse was not the case.

The arrival of sulfur hexafluoride alone at some of the wells suggests the following explanations:
1. The sulfur hexafluoride has greater mobility than the chloropentafluoroethane;
2. The chloropentafluoroethane was diluted to concentrations below its detectability; or
3. Low permeability of the underground structures restricted the migration of chloropentafluoroethane preventing concentrations at detectable levels from moving to the sampling sites.

It is believed that while chloropentafluoroethane shows fair mobility characteristics, the structure of the rock in the area of the wells at which chloropentafluoroethane was not detected may have prevented the permeation of the chloropentafluoroethane to those points. This leads to the conclusion that sulfur hexafluoride is a better tracer gas than chloropentafluoroethane, while chloropentafluoroethane is still a practical tracer in many of the underground reservoir sites that are now in existance. The initial detection of the tracer gases at withdrawal wells before withdrawal began is primarily due to conduction due to pressure drops through the reservoir and by diffusion due to concentration gradients existing within the reservoir. This indicates that in fact the tracers were more than capable of diffusing into the untagged gases.

The test analyses of the samples was conducted by a mobile gas chromatograph system of the electron capture variety; however, back-up confirmation samples were taken to the laboratores and analyzed on the same equipment described in Example I above.

When the withdrawal period began after 1 billion cubic feet of gas had been produced from the storage, analysis was conducted at all of the wells. Sulfur hexafluoride was detected at every well throughout the withdrawal sampling period over a period of two months. Because of the remoteness of the field from the laboratory the tests of the wells for tracer concentrations were conducted only every two weeks. The fact that tracers were detected immediately upon analysis following the withdrawal of 1 billion cubic feet from storage suggests that the tracers were well diffused and mixed into the 7.7 billion cubic feet of untagged gas. Additionally testing continued while an additional 9.2 billion cubic feet of gas were removed from storage. The sulfur hexafluoride and chloropentafluoroethane remained available in detectable concentrations throughout this withdrawal. Considering that a total of 9.12 cubic feet of sulfur hexafluoride vapor (3.5 pounds, or 1.5 kilogram of liquid) were injected into the 10.5 billion cubic feet of gas by means of the 2.8 billion foot spiking sample, the total concentration in the gas would be 0.87 ppb. The data obtained showed average concentrations of sulfur hexafluoride ranging from 0.7 to 1.3 ppb during the entire withdrawal period. This again confirms that the diffusion of the sulfur hexafluoride into the greater body of gas was very complete and that even small concentration gradients were capable of being eliminated by this highly mobile tracer. This same analysis was not able to be performed on the chloropentafluoroethane because the concentrations were more erratic probably due to the lower permeability to that tracer in the underground structure that was tested at this time. Areas of low permeability will have had very little tracer conducted or diffused through them thereby allowing areas of higher permeability to have even higher concentrations. The overall concentration averages then depend on the mix of withdrawal wells in the main line at the time of sampling. However, the chloropentafluoroethane was clearly shown to have good migration characteristics within the reservoir.

There are certain conditions which render the use of the instant tracer compounds in underground gas storage fields more difficult. For example, since all the tracer compounds (as well as the prior art tracer ethylene) have some solubility in petroleum distillates, where such distillates are present in a gas storage field the distillates will absorb some of the tracer making the tracer more difficult to detect. In some circumstances it may be desirable to increase the tracer concentrations in order to allow for losses of tracer to distillates. Laboratory tests establish that sulfur hexafluoride has a solubility in petroleum distillates about equal to that of the prior art tracer ethylene, while chloropentafluoroethane is slightly more soluble than ethylene in petroleum distillates. In addition, when tagging gas being pumped into large gas storage fields, care should be taken to avoid excessive dilution of the tagged gas with untagged gas, to a point at which the tracers fall below detectable concentrations. For example, in Example 1 above, approximately 4.2 million standard cubic feet of tagged methane were injected into a field of 1.2 billion standard cubic foot capacity; thus, the tagged gas amounted to 0.35% of the field's capacity. As described above, the tests set forth in Example 1 produced highly acceptable results. In contrast, in one unsuccessful experiment 17 million standard cubic feet of tagged gas containing (on average) two parts per billion of sulfur hexafluoride and 2.1 part per million of chloropentafluoroethane were injected into a field having a capacity of 23.7 billion standard cubic feet which contained some light oils and petroleum distillates; thus the tagged portion of gas amounted to only 0.07% of the capacity of the field. Following injection of this tagged gas an additional 25 million standard cubic feet of untagged gas was pumped into the field via the same well. Tests for the tracer compounds were conducted at the gas issuing from a production well approximately one half mile from the injection well over a period of seven months but no trace of the compounds was detected. Also, tests at several other withdrawal wells in the same gas storage field proved negative after seven months. Finally, when after seven months gas was withdrawn from the injection well, sulfur hexafluoride was detected in the gas withdrawn at a level of 1.1 parts per billion, only 0.13 percent of the injection level (allowing for dilution of the sulfur hexafluoride by the untagged gas which was followed after the tagged gas, the injection level of sulfur hexafluoride was 840 parts per billion). During continued withdrawal from the injection well, the concentration of sulfur hexafluoride rose only to ten parts per billion, 1.2% of the injection level.

The relative lack of success of this test may be due in some degree to the absorption of the tracers into the distillates present in the gas field, but is likely that the major factor accounting for the relative lack of success is excessive dilution of the tagged gas injected by the much larger quantities of gas already present in the very large field. Absorption of the tracers into formations present in the field and adjacent areas may also play some part in the failure of t his test.

It will be appreciated that numerous changes and modifications may be made in the above-described embodiments of the invention without departing from the scope thereof. Accordingly, the foregoing description is to be construed in an illustrative and not in a limitative sense, the scope of the invention being defined solely by the appended claims.

We claim:

1. Apparatus for injecting a tracer mixture into a pipeline leading to an underground storage field, comprising:
    a source of gas,
    a pipeline in fluid communication with said source of gas at one end and at the other end with an underground gas storage field, and with gas flowing in said pipeline toward the field,
    a branch line leading from said pipeline to conduct gas from said pipeline to a fluid pump and the flow and pressure of said gas driving said pump,
    a container of a tracer mixture connected in fluid communication with said pump,
    means forming a conduit from said pump to said pipeline for delivering said tracer mixture to the pipeline, the location of the connection of the conduit with the pipeline being downstream from the location of the branch line connection with the pipeline and
    means for (1) detecting the flow of the tracer mixture in the conduit and (2) signaling when no mixture is flowing.

2. The apparatus of claim 1 wherein the gas in the pipeline is at a pressure of about 600 to 1400 psig,
    means for reducing the pressure of the gas in the branch line to about 75 psig.

3. The apparatus of claim 2 wherein the tracer mixture is a liquid mixture of carbon dioxide and sulfur hexafluoride.

4. The apparatus of claim 2 wherein the tracer mixture is liquid chloropentafluoroethane.

5. The apparatus of claim 1 wherein said tracer mixture is a liquid mixture of carbon dioxide and sulfur hexafluoride.

6. The apparatus of claim 5 wherein the container is maintained at a pressure of not less than about 900 psig.

7. The apparatus of claim 1 wherein the tracer mixture is liquid chloropentafluoroethane.

8. The apparatus of claim 1 including means forming an accumulator for reducing the pressure variations in the conduit means, said accumulator means being in fluid communication with said conduit means at a location between said fluid pump and said pipeline.

9. The apparatus of claim 8 including a return line from said conduit to said container, a pressure regulator means in fluid communication with said return line for controlling the return flow of tracer mixture from said conduit to said container.

10. Apparatus for injecting a tracer mixture into a pipeline leading to an underground storage field, comprising:
    a gas flowing under pressure in said pipeline toward said storage field,
    a container of tracer mixture, said mixture being a gaseous mixture of nitrogen and sulfur hexafluoride,
    a conduit in fluid communication with said container and said pipeline, the container being at a pressure greater than the pressure in the pipeline,
    means for controlling the quantity of mixture injected into said pipeline based on the flow of gas in said pipeline,
    means in said conduit for reducing the pressure of said mixture to a pressure suitable for injection into said pipeline.

11. Apparatus for injecting tracer mixtures into a pipeline leading to an underground storage field, comprising:
    a gas flowing under pressure in said pipeline toward said storage field,
    a branch line leading from said pipeline to conduct gas from said pipeline to at least two fluid pumps,
    at least two containers of tracer mixtures, each container holding a different tracer mixture, each container being in fluid communication with one of said fluid pumps,
    conduit means leading from each pump to a junction where the conduit means merge into a single flow path leading to said pipeline,
    means for controlling the flow of tracer mixture from each container based upon the flow rate in the pipeline.

12. The apparatus of claim 11 wherein the containers hold a tracer mixture selected from the group consisting of sulfur hexfluoride, chloropentafluoroethane and ethylene.

13. The apparatus of claim 12 wherein the container holding the chloropentafluoroethylene is at a pressure of about 120 psig and the chloropentafluoroethane is in liquid form.

14. The apparatus of claim 12 wherein the gas in the pipeline is about 1000 psig and the tracer mixture is raised to a pressure of about 1500 psig prior to insertion into the pipeline.

* * * * *